US012611476B2

(12) United States Patent     (10) Patent No.:   US 12,611,476 B2

Ufkes et al.     (45) Date of Patent:    Apr. 28, 2026

(54) APPARATUS, SYSTEM AND METHOD FOR ADAPTIVE EMISSION OF RADIATION IN INTERIOR ENVIRONMENTS

(71) Applicant: UD Innovations, LLC, Sullivan's Island, SC (US)

(72) Inventors: Philip J. Ufkes, Sullivan's Island, SC (US); Jeffery L. Deal, Charleston, SC (US)

(73) Assignee: UD Innovations, LLC, Sullivan's Island, SC (US)

( * ) Notice: Subject to any disclaimer, the term of this patent is extended or adjusted under 35 U.S.C. 154(b) by 903 days.

(21) Appl. No.: 17/495,658

(22) Filed: Oct. 6, 2021

(65) Prior Publication Data

US 2022/0105220 A1     Apr. 7, 2022

Related U.S. Application Data

(60) Provisional application No. 63/088,418, filed on Oct. 6, 2020.

(51) Int. Cl.
    *A61L 2/26*       (2006.01)
    *A61L 2/10*       (2006.01)

(52) U.S. Cl.
    CPC    *A61L 2/26* (2013.01); *A61L 2/10* (2013.01); *A61L 2202/14* (2013.01); *A61L 2202/25* (2013.01)

(58) Field of Classification Search
    CPC .......... A61L 2/10; A61L 2/26; A61L 2202/14; A61L 2202/25; A61L 2209/111; A61L 9/20
    See application file for complete search history.

(56) References Cited

U.S. PATENT DOCUMENTS

| | | | | |
|---|---|---|---|---|
| 2017/0246331 A1* | 8/2017 | Lloyd | .................... | A61Q 17/04 |
| 2018/0193501 A1* | 7/2018 | Ufkes | ...................... | A61L 2/10 |
| 2018/0321790 A1* | 11/2018 | Cohen | .................. | G06F 3/0416 |
| 2019/0117812 A1* | 4/2019 | Olsen | ....................... | A61L 2/26 |
| 2021/0018884 A1* | 1/2021 | Kupa | .................. | H05B 47/115 |
| 2021/0052757 A1* | 2/2021 | Baarman | ............... | G16H 10/60 |
| 2023/0149578 A1* | 5/2023 | Igarashi | .............. | A61N 5/0624 422/3 |
| 2023/0248862 A1* | 8/2023 | Benner | .................... | A61L 2/10 422/24 |

* cited by examiner

*Primary Examiner* — Brendan A Hensel

(74) *Attorney, Agent, or Firm* — Gregory Finch; Finch Paolino, LLC

(57) ABSTRACT

A germicidal disinfection apparatus, system and method. Embodiments of the present disclosure include an adaptive germicidal disinfection apparatus, system and method comprising one or more sensors communicably engaged with a controller being configured to control the operation of at least one UV-C emitter. The sensors may be configured to detect various signals from an interior environment and communicate such signals as inputs to the controller. The controller may be configured to process the inputs according to one or more data processing framework to assess and determine a variety of disease control risk factors and trigger conditions. The controller may be configured to configure one or more modes of operation for the at least one UV-C emitter according to an output of one or more data processing operations.

6 Claims, 11 Drawing Sheets

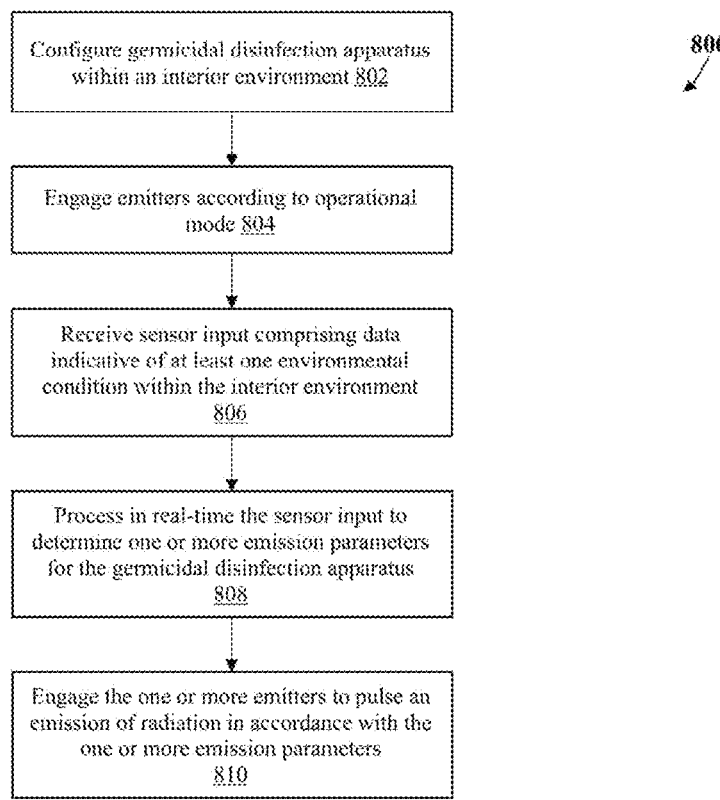

Configure germicidal disinfection apparatus within an interior environment 802

Engage emitters according to operational mode 804

Receive sensor input comprising data indicative of at least one environmental condition within the interior environment 806

Process in real-time the sensor input to determine one or more emission parameters for the germicidal disinfection apparatus 808

Engage the one or more emitters to pulse an emission of radiation in accordance with the one or more emission parameters 810

APPARATUS, SYSTEM AND METHOD FOR ADAPTIVE EMISSION OF RADIATION IN INTERIOR ENVIRONMENTS

CROSS-REFERENCE TO RELATED APPLICATIONS

This application claims priority benefit of U.S. Provisional Application Ser. No. 63/088,418 filed Oct. 6, 2020, the entirety of which is hereby incorporated herein at least by reference.

FIELD

The present disclosure relates to the field of germicidal disinfection systems that utilize ultraviolet light; in particular, an apparatus, system and method for adaptive emission of ultraviolet radiation in interior environments based on real-time sensor data and external data feeds.

BACKGROUND

Ultraviolet germicidal irradiation (UVGI) is a disinfection method that uses short-wavelength ultraviolet (UV-C) light to kill or inactivate microorganisms. One mechanism by which UV-C deactivates microorganisms is by destroying nucleic acids and disrupting their DNA, leaving them unable to perform vital cellular functions. The administration of UV-C radiation is becoming widely adopted by many hospitals as a more effective and reliable means of surface disinfection, as compared to the use of chemical cleaning agents alone. The effectiveness of germicidal UV-C irradiation depends on factors such as the length of time a microorganism is exposed to UV-C, the intensity and wavelength of the UV-C radiation, the presence of particles that can protect the microorganisms from UV, and a microorganism's ability to withstand UV-C during its exposure. In air and surface disinfection applications, the UV effectiveness is estimated by calculating the UV dose to be delivered to the microbial population. A method of calculating UV dose is as follows: UV dose $\mu Ws/cm^2$=UV intensity $\mu W/cm^2 \times$Exposure time (seconds).

Germicidal UV for disinfection is most typically generated by a mercury-vapor lamp. Low-pressure mercury vapor has a strong emission line at 254 nm, which is within the range of wavelengths that demonstrate strong disinfection effect. The optimal wavelengths for disinfection are close to 265 nm, although recent data has suggested that Far-UVC light (i.e., 207-222 nm) efficiently inactivates microorganisms without harm to exposed mammalian skin. (See Welch D, Buonanno M, Grilj V, et al. *Far-UVC light: A new tool to control the spread of airborne-mediated microbial diseases.* Sci Rep. 2018; 8(1):2752. 2018 Feb. 9.) UV-C LEDs use semiconductors to emit light between 207 nm-280 nm. The wavelength emission is tunable by adjusting the material of the semiconductor. The use of LEDs that emit a wavelength more precisely tuned to the maximal germicidal wavelength results in greater microbe deactivation per amp of power, maximization of microbial deactivation, less ozone production, and less materials degradation. Various prior art solutions have been presented to enable the selective transmission of UV-C radiation for the purpose of inactivating microorganisms present in the air and on surfaces within an interior environment.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Certain aspects of the present disclosure provide for a germicidal disinfection apparatus comprising a housing configured to be selectively coupled to a surface of an interior room of a building; a plurality of emitters housed within the housing, the plurality of emitters comprising at least one emitter configured to pulse an emission of ultraviolet radiation at a wavelength in the range of 200 nm to 405 nm; a one or more sensors housed within the housing, the one or more sensors comprising at least one sensor configured to detect the presence of one or more occupants within the interior room of the building; and a controller housed within the housing and operably engaged with the plurality of emitters and the one or more sensors, wherein the controller is configured to receive and process an input from the one or more sensors to determine at least one risk factor for person-to-person transmission of at least one microorganism and configure one or more control parameters for the plurality of emitters to pulse an emission of ultraviolet radiation in response to the determined at least one risk factor.

In accordance with certain embodiments of the germicidal disinfection apparatus, the one or more sensors may be selected from the group consisting of cameras, acoustic transducers, microphones, radiation sensors, passive infrared sensors, temperature sensors, humidity sensors and carbon dioxide sensors. In certain embodiments, the germicidal disinfection apparatus is configured wherein determining the at least one risk factor for person-to-person transmission of at least one microorganism comprises processing, with the controller, the input from the one or more sensors to determine an occupant density for the interior room of the building. In certain embodiments, the germicidal disinfection apparatus is configured wherein determining the at least one risk factor for person-to-person transmission of at least one microorganism comprises processing, with the controller, the input from the one or more sensors to determine an occurrence of a microorganism transmission event within the interior room of the building, wherein the microorganism transmission event comprises a cough or sneeze from at least one occupant present in the interior room of the building. In certain embodiments, the germicidal disinfection apparatus is configured wherein the controller is further configured to pulse the emission of ultraviolet radiation in response to the occupant density for the interior room of the building exceeding a predetermined threshold value. In certain embodiments, the germicidal disinfection apparatus is configured wherein the controller is further configured to pulse the emission of ultraviolet radiation, in real time, in response to determining the occurrence of the microorganism transmission event within the interior room of the building. In certain embodiments, the germicidal disinfection apparatus is configured wherein the plurality of emitters comprises a first emitter configured to pulse a first emission of ultraviolet radiation at a first wavelength in the range of 200 nm to 405 nm and a second emitter configured to pulse a second emission of ultraviolet radiation at a second wavelength in the range of 200 nm to 405 nm, wherein the first wavelength is different from the second wavelength.

Further aspects of the present disclosure provide for a germicidal disinfection system comprising a plurality of emitters comprising at least one emitter configured to pulse an emission of ultraviolet light at a wavelength in the range of 200 nm to 405 nm; one or more sensors comprising at least one sensor configured to detect the presence of one or more occupants within an interior environment; a controller communicably engaged with the plurality of emitters and the one or more sensors, wherein the controller is configured to receive and process an input from the one or more sensors to determine at least one risk factor for person-to-person transmission of at least one microorganism within the interior environment and configure one or more control parameters for the plurality of emitters to pulse an emission of ultraviolet light within the interior environment; and a remote server communicably engaged with the controller via at least one network interface, wherein the remote server is configured to transmit data to the controller to configure the one or more control parameters for the plurality of emitters and receive activity data from the controller comprising real-time or historical emission data and sensor data.

In accordance with certain embodiments of the germicidal disinfection apparatus, the one or more sensors are selected from the group consisting of cameras, acoustic transducers, microphones, radiation sensors, passive infrared sensors, temperature sensors, humidity sensors and carbon dioxide sensors. In certain embodiments, the germicidal disinfection apparatus is configured wherein determining the at least one risk factor for person-to-person transmission of at least one microorganism comprises processing, with the controller, the input from the one or more sensors to determine an occupant density for the interior room of the building. In certain embodiments, the germicidal disinfection apparatus is configured wherein determining the at least one risk factor for person-to-person transmission of at least one microorganism comprises processing, with the controller, the input from the one or more sensors to determine an occurrence of a microorganism transmission event within the interior room of the building, wherein the microorganism transmission event comprises a cough or sneeze from at least one occupant present in the interior room of the building. In certain embodiments, the germicidal disinfection apparatus is configured wherein determining the at least one risk factor for person-to-person transmission of at least one microorganism comprises processing, with the remote server, at least one public health data input associated with a rate or prevalence of transmission of the at least one microorganism in a geographic location associated with the interior environment. In certain embodiments, the germicidal disinfection apparatus is configured wherein the controller is further configured to pulse the emission of ultraviolet radiation in response to the occupant density for the interior room of the building exceeding a predetermined threshold value. In certain embodiments, the germicidal disinfection apparatus is configured wherein the controller is further configured to pulse the emission of ultraviolet radiation, in real time, in response to determining the occurrence of the microorganism transmission event within the interior room of the building. In certain embodiments, the germicidal disinfection apparatus is configured wherein the plurality of emitters comprises a first emitter configured to pulse a first emission of ultraviolet radiation at a first wavelength in the range of 200 nm to 405 nm and a second emitter configured to pulse a second emission of ultraviolet radiation at a second wavelength in the range of 200 nm to 405 nm, wherein the first wavelength is different from the second wavelength.

Still further aspects of the present disclosure provide for a method for germicidal disinfection comprising configuring the germicidal disinfection apparatus in a location within an interior environment; receiving, with the one or more sensors, at least one sensor input comprising data indicative of at least one environmental condition within the interior environment, wherein the at least one environmental condition comprises at least one risk factor for person-to-person transmission of at least one microorganism between two or more occupants present within the interior environment; processing in real-time, with the controller, the at least one sensor input to determine one or more emission parameters for the germicidal disinfection apparatus; and engaging, with the controller, the plurality of emitters to pulse an emission of radiation in accordance with the one or more emission parameters, wherein the emission of radiation comprises an emission of ultraviolet light having a wavelength in the range of 200 nm to 405 nm.

In accordance with certain aspects of the present disclosure, the method for germicidal disinfection may further comprise processing in real-time, with the controller, the at least one sensor input to determine an occupant density for the interior room of the building. In accordance with certain aspects of the present disclosure, the method for germicidal disinfection may further comprise processing in real-time, with the controller, the at least one sensor input to determine an occurrence of a microorganism transmission event within the interior room of the building, wherein the microorganism transmission event comprises a cough or sneeze from at least one occupant present in the interior room of the building. In accordance with certain aspects of the present disclosure, the method for germicidal disinfection may further comprise engaging, with the controller, the plurality of emitters to pulse the emission of radiation in response to the occupant density for the interior room of the building exceeding a predetermined threshold value. In accordance with certain aspects of the present disclosure, the method for germicidal disinfection may further comprise engaging, with the controller, the plurality of emitters to pulse the emission of radiation, in real time, in response to determining the occurrence of the microorganism transmission event within the interior room of the building.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which:

FIG. 8 is a process flow diagram of a method for adaptive germicidal disinfection of an interior environment, in accordance with certain aspects of the present disclosure.

DETAILED DESCRIPTION

Figure 1:
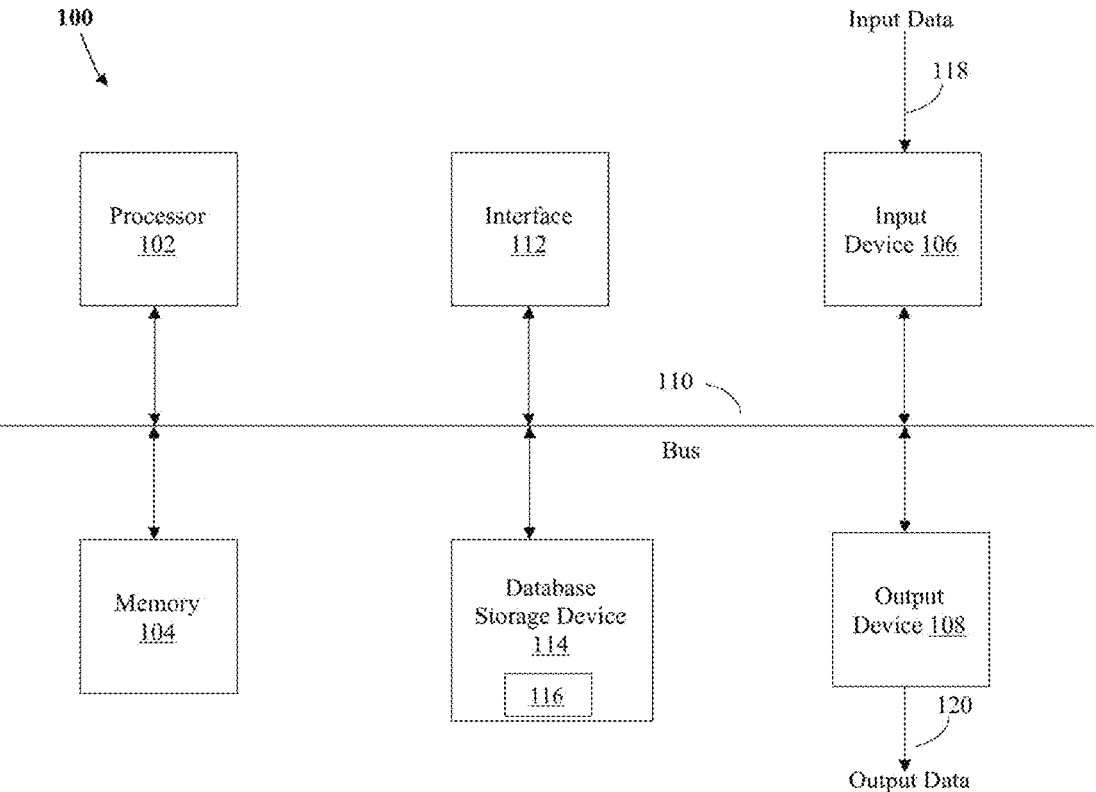
FIG. 1 is an illustrative embodiment of a computing device through which one or more aspects of the present disclosure may be implemented.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems configured to provide for real-time, adaptive UV-C germicidal disinfection within interior environments. Embodiments of the present disclosure may provide for one or more sensors configured to detect various signals from an interior environment and communicate such signals as inputs to a controller. The controller may be configured to process the inputs according to one or more data processing framework to assess and determine a variety of disease control risk factors and trigger conditions for the interior environment and occupants therein. The controller may be configured to configure one or more modes of operation to pulse an emission of radiation from at least one UV-C emitter according to an output of one or more data processing operations.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

As used herein, the term "interface" refers to any shared boundary across which two or more separate components of a computer system may exchange information. The exchange can be between software, computer hardware, peripheral devices, humans, and combinations thereof An exemplary system, method, and apparatus according to the principles herein may include an adaptive germicidal disinfection system comprising two or more adaptive germicidal disinfection apparatuses communicably engaged over a local area network or a wide area network. An adaptive germicidal disinfection apparatus may be configured to be installed to a ceiling of an interior room of a building.

An exemplary system, method, and apparatus according to the principles herein may include an adaptive germicidal disinfection system comprising one or more emitters configured to emit radiation at one or more wavelengths in response to a command operation from at least one controller. The controller may be configured to configure one or more modes of operation for the adaptive germicidal disinfection system to control an emission of radiation (e.g., light) from the one or more emitters. In certain exemplary embodiments, the one or more modes of operation may include controlling an emission from the one or more emitters to enable emission of a single band of radiation, a dual band of radiation or a multi-band of radiation. The one or more modes of operations may also include modulating a duty cycle of the emitters to control the intensity and phase of emission.

An exemplary system, method, and apparatus according to the principles herein may include an adaptive germicidal disinfection system comprising one or more sensors communicably engaged with a controller configured to control the operation of a plurality of emitters. The sensors may include one or more of a camera such as a digital video or digital still image camera, an acoustic transducer, a radiation sensor, an occupant sensor such as a passive infrared sensor, and environmental sensors, such as temperature, humidity and $CO_2$ sensors configured detect a change in an environment due to the presence of a human. The sensors may be configured to detect various signals from an interior environment and communicate such signals as inputs to the controller. The controller may be configured to process the inputs according to one or more data processing framework to assess and determine a variety of disease control risk factors and trigger conditions. The controller may be configured to configure one or more modes of operation for the plurality of emitters according to the outcome of processing the sensor inputs.

An exemplary system, method, and apparatus according to the principles herein may include an adaptive germicidal disinfection system comprising a remote server and/or a building information system and/or a client device communicably engaged with a controller configured to control the operation of a plurality of emitters. The remote server and/or the building information system and/or the client device may be communicably engaged with the controller to communicate one or more data inputs and/or command signals to the controller. The data inputs and/or command signals may include: public health data or other infection control data, such as weather or local disease activity data; internal system data, such as emission data and disinfection status; building information data, such as building occupancy data, HVAC data; and data associated with user-generated inputs, such as operational settings/commands, and disinfection data such as timing and location of the application of chemical cleaning agents. The remote server and/or the building information system and/or the client device may be communicably engaged with the controller to receive one or more data packets from the controller according to one or more communication protocols. Data communicated from the controller to the remote server and/or the building information system and/or the client device may be processed according to one or more data processing framework in order to take one or more infection control and/or disease prevention actions.

In accordance with an exemplary use case provided by embodiments of the present disclosure, an adaptive germicidal disinfection apparatus and system may be installed in an interior room or location of a building; for example, an airport terminal or a waiting room in a hospital. The adaptive germicidal disinfection apparatus and system may comprise one or more sensors configured to detect one or more input signals associated with human presence within the interior room or location of the building. The adaptive germicidal disinfection apparatus and system may include an acoustic transducer (e.g., a microphone) configured to receive an acoustic audio input and communicate the acoustic audio input as a signal to the controller. The controller may process the audio input according to one or more audio processing operations to determine one or more spectral and/or temporal characteristics of the signal to identify the presence of a human cough or sneeze generated by an occupant within the interior room or location of the building. The controller may utilize one or more audio processing functions to approximate a location of the cough or sneeze from within the interior room or location; for example, applying an acoustic propagation model to the input signal or comparing an amplitude of the input signal to a reference signal from an input channel associated with a known location. The controller may further process the output of the audio processing function in real-time to configure and pulse an emission of UV-C radiation within a target emission zone to inactivate airborne microorganisms and pathogens emanating from the sneeze or cough.

In further exemplary use cases, the adaptive germicidal disinfection apparatus and system may be configured to determine an occupant load within the interior room or location of the building to assess one or more risk factors for disease transmission. The adaptive germicidal disinfection apparatus and system may communicate with a building information system or client device to adaptively modify a recommended maximum occupant load for the interior room or location and/or provide a notification when social distancing guidelines are not being observed.

In further exemplary use cases, the adaptive germicidal disinfection apparatus and system may be configured to process environmental sensor input according to one or more data processing frameworks to assess one or more disease transmission risk factors. In an exemplary use case, the adaptive germicidal disinfection apparatus may be configured to analyze the temperature and humidity of an interior location relative to the number of occupants present within the location to determine the likelihood and risk of one or more of the occupants being sick.

Certain benefits and advantages of the present disclosure include a system, method, and apparatus that can detect the transmission of airborne microorganisms and pathogens in real-time and pulse an emission of UV-C radiation to a target area to inactivate the airborne microorganisms and pathogens.

Certain benefits and advantages of the present disclosure include a system, method, and apparatus configured to measure and evaluate environmental conditions of an interior environment in real-time to assess one or more risk factors for disease transmission. Further benefits include a system and method for processing real-time environmental data, historical data and/or external data according to a machine learning framework to provide one or more recommendations for controlling or preventing the disease transmission.

Certain benefits and advantages of the present disclosure include a system, method, and apparatus configured to measure and evaluate environmental conditions of an interior environment, occupant load and occupant movement in order to provide more robust public health and infection control data.

Turning now descriptively to the drawings, in which similar reference characters denote similar elements throughout the several views, FIG. 1 depicts an exemplary computing system in which certain illustrated embodiments of the present invention may be implemented.

Referring now to FIG. 1, a processor-implemented computing device in which one or more aspects of the present disclosure may be implemented is shown. According to an embodiment, a processing system 100 may generally comprise at least one processor 102, or processing unit or plurality of processors, memory 104, at least one input device 106 and at least one output device 108, coupled together via a bus or group of buses 110. In certain embodiments, input device 106 and output device 108 could be the same device. An interface 112 can also be provided for coupling the processing system 100 to one or more peripheral devices, for example interface 112 could be a PCI card or PC card. At least one storage device 114 which houses at least one database 116 can also be provided. The memory 104 can be any form of memory device, for example, volatile or non-volatile memory, solid state storage devices, magnetic devices, etc. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 10a and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which embodiments of the below described present invention may be implemented. FIG. 1 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system environment 100 of FIG. 1. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, set top boxes, programmable consumer electronics, network, minicomputers, server computers, game server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

With the exemplary computing system environment 100 of FIG. 1 being generally shown and discussed above, description will now turn towards illustrated embodiments of the present invention which generally relates to methods for data processing and communication protocols within a germicidal disinfection apparatus and system.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either/both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

Any publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

Figure 2:
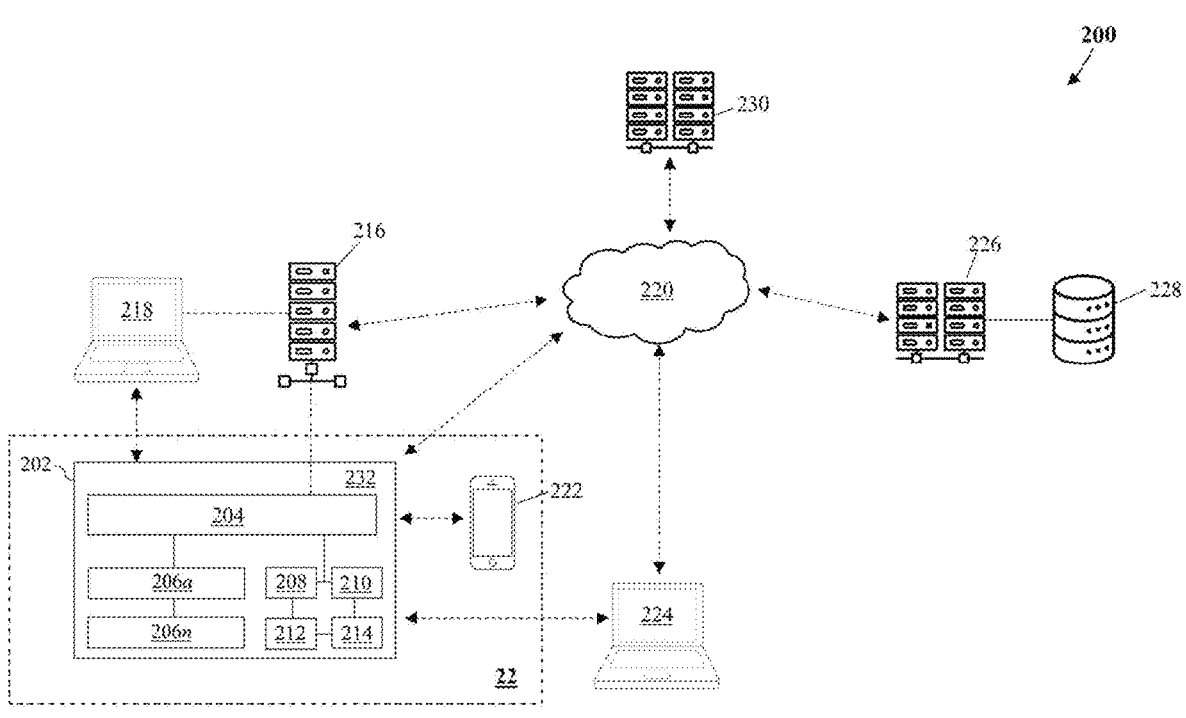
FIG. 2 is an architecture diagram of an adaptive germicidal disinfection system, in accordance with certain aspects of the present disclosure.

Referring now to FIG. 2, an architecture diagram of an adaptive germicidal disinfection system 200 is shown. In accordance with certain aspects of the present disclosure, adaptive germicidal disinfection system 200 is comprised of a germicidal disinfection apparatus 202 installed in an interior environment 22 and communicably engaged with one or more of a client device 222, a client device 224, an administrator client 218 and/or a local server 216. Germicidal disinfection apparatus 202 may be communicably engaged with a remote server 226 via a communications network 220. Communications network 220 may comprise an Internet connection and/or wireless data network connection (e.g., 4G or 5G). In certain embodiments, remote server 226 may be communicably engaged with a database 228. Adaptive germicidal disinfection system 200 may further comprise one or more third-party server 230. In certain embodiments, third-party server 230 may be communicably engaged with remote server 226 and/or local server 216 via communications network 220 to send and receive data.

In accordance with certain embodiments, germicidal disinfection apparatus 202 may be comprised of a housing 232, a controller 204, a first plurality of emitters 206a, a second plurality of emitters 206n, and one or more of a camera or optical sensor 208, an acoustic transducer 210, an environmental sensor 212 and a radiation sensor 214. In accordance with certain aspects of the present disclosure, housing 232 may be configured to be coupled to a ceiling of an interior room of a building comprising interior environment 22. In certain embodiments, housing 232 may be configured to connect to a standard electrical junction box and/or be installed within a ceiling grid of a drop ceiling. Housing 232 may comprise electrical connections to provide power from the electrical wiring of the building to the other elements of germicidal disinfection apparatus 202. Controller 204 may comprise a processor, memory device and circuitry to control the flow and transmission of data and power to and from the other elements of germicidal disinfection apparatus 202. Controller 204 may also comprise a transceiver and other communications circuitry to enable a wireless or wireline bi-directional communications interface between controller 204 and the other components of germicidal disinfection system 200. In accordance with certain aspects of the present disclosure, emitters 206a may comprise one or more emitters optionally comprising an array. Emitters 206a may comprise light-emitting diode (LED) emitters configured to produce an emission of light in the UV-C spectral range (i.e., a wavelength of 100 nm to 280 nm). Emitters 206a may comprise one or more emitters configured to emit a first wavelength of UV-C light (e.g., 222 nm) and one or more emitter configured to emit a second wavelength of UV-C light (e.g., 264 nm). Emitters 206n may also comprise LED emitters and may be configured to produce an emission of light at a wavelength ranging from ultraviolet to visible light to infrared. According to various embodiments, germicidal disinfection apparatus 202 may comprise multiple sets of emitters 206a-206n comprising multiple emitters and/or emitter types configured to emit radiation at different wavelengths. Controller 204 may be operably engaged with emitters 206a-206n to selectively pulse radiation from emitters 206a-206n and control the duty cycle of emitters 206a-206n to modulate the duty cycle, phase, intensity and operation of emitters 206a-206n. In accordance with further aspects of the present disclosure, camera or optical sensor 208, acoustic transducer 210 and environmental sensor 212 may be configured to detect one or more input signals associated with human occupants present within interior environment 22. Camera or optical sensor 208, acoustic transducer 210 and environmental sensor 212 may be communicably engaged with controller 204 to communicate sensor data from the one or more input signals to the processor of controller 204. Controller 204 may be configured to process the sensor data according to one or more data processing frameworks in order to configure one or more operations of the processor.

In accordance with certain aspects of the present disclosure, controller 204 may be communicably engaged with local server 216 and/or administrator client 218 to receive one or more system configurations, operational commands and/or provisioning of software. Controller 204 may be further configured to communicate real-time or historical system data to local server 216 and/or administrator client 218, such as emission data and sensor data. Controller 204 may be configured to execute one or more data processing operations locally and/or may communicate emission data and/or sensor data to local server 216 and/or administrator client 218 to perform one or more data processing operations and, optionally, communicate an output of said operations back to controller 204. Local server 216 may be communicably engaged with remote server 226 and/or third-party server 230 to receive external data, such as weather data and public health/disease activity data for a geographic location associated with interior environment 22. Controller 204 may be communicably engaged with remote server 226 to receive one or more system configurations, operational commands and/or provisioning of software. Controller 204 and/or local server 216 may be further configured to communicate real-time or historical system data to remote server 226, such as emission data and sensor data. Remote server 226 may be configured to receive data from controller 204 and/or local server 216, process data according to one or more data processing framework and, optionally, communicate an output of said the data processing framework back to controller 204 and/or local server 216. Controller 204 may be communicably engaged with client device 222, client device 224 and/or administrator client 218 to communicate real-time or historical system data, such as emission data and sensor data, and/or one or more system recommendations based on the output of one or more data processing framework. Client device 222, client device 224 and/or administrator client 218 may be configured to render at least one graphical user interface to display the data and/or recommendations and enable one or more user-generated inputs.

Figure 3:
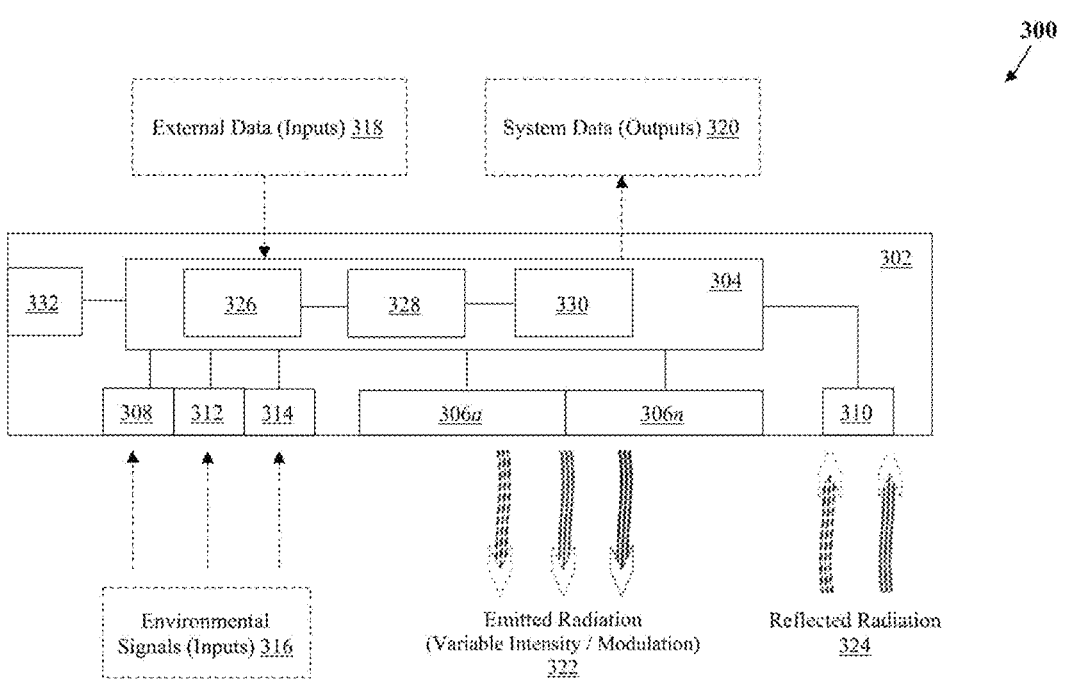
FIG. 3 is a functional block diagram of an adaptive germicidal disinfection apparatus, in accordance with certain aspects of the present disclosure.
Figure 4A:
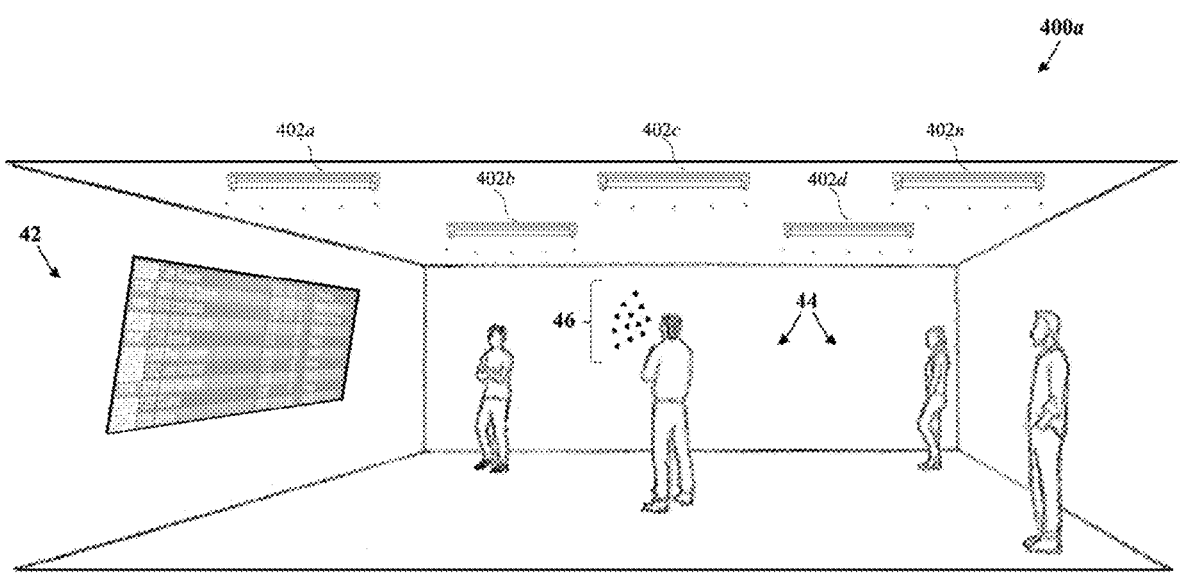
FIG. 4A is a functional diagram of an adaptive germicidal disinfection system, in accordance with certain aspects of the present disclosure.
Figure 4B:
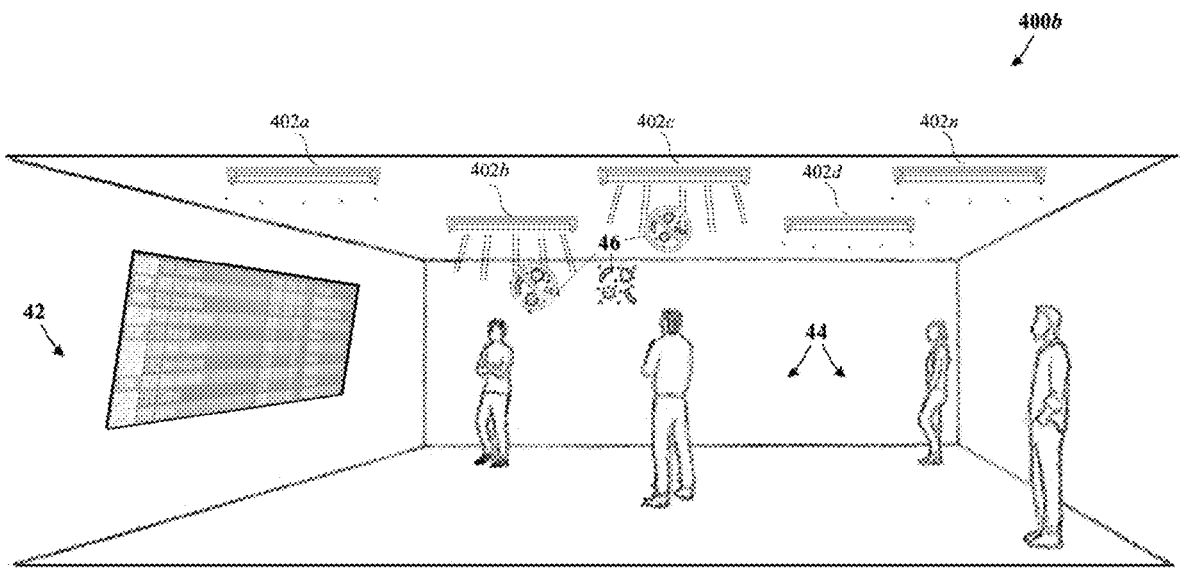
FIG. 4B is a functional diagram of an adaptive germicidal disinfection system, in accordance with certain aspects of the present disclosure.
Figure 4C:
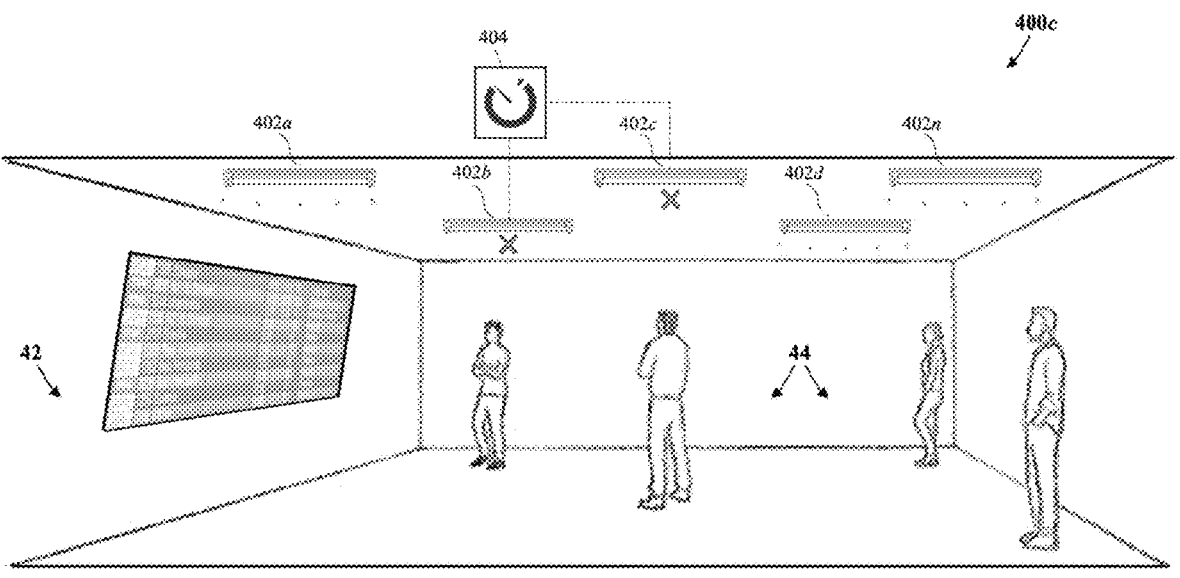
FIG. 4C is a functional diagram of an adaptive germicidal disinfection system, in accordance with certain aspects of the present disclosure.
Figure 4D:
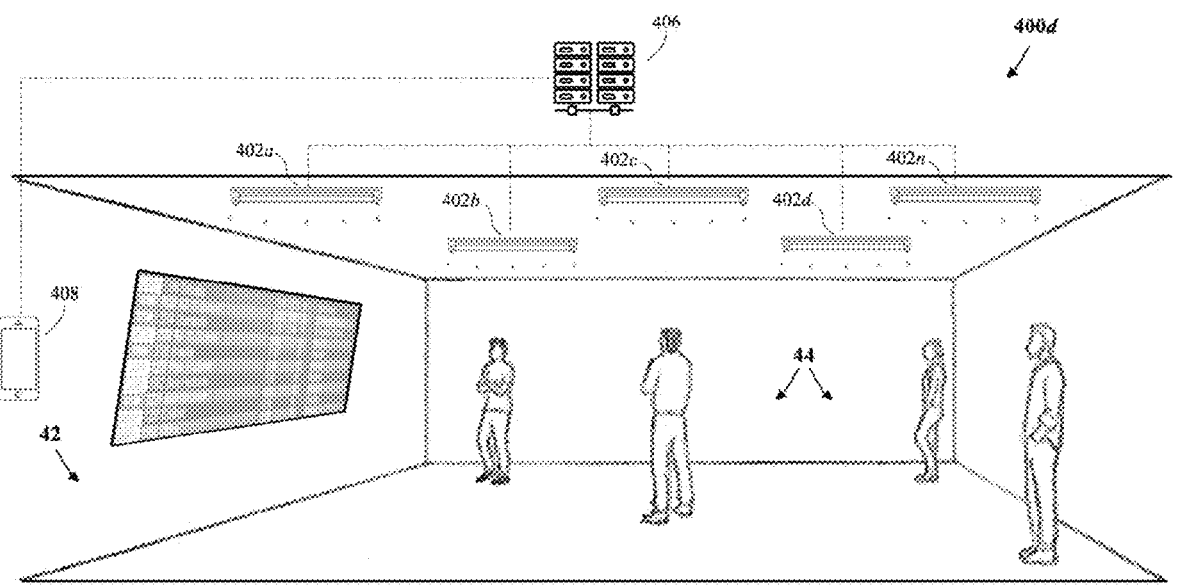
FIG. 4D is a functional diagram of an adaptive germicidal disinfection system, in accordance with certain aspects of the present disclosure.

Referring now to FIG. 3 (with reference to FIG. 2), a functional block diagram of an adaptive germicidal disinfection apparatus 300 is shown. In accordance with certain aspects of the present disclosure, germicidal disinfection apparatus 300 may comprise germicidal disinfection apparatus 202 of FIG. 2 and/or may otherwise be incorporated into germicidal disinfection system 200 of FIG. 2. In accordance with certain embodiments, germicidal disinfection apparatus 300 may comprise a housing 302 configured to house the other components of germicidal disinfection apparatus 300. Housing 302 may be configured to be installed to a ceiling of an interior room of a building and may be interfaced with electrical wiring of the building via power supply 332. Power supply 332 may be configured to receive an electrical current from the electrical wiring of the building to provide power to the other elements of germicidal disinfection apparatus 300. In accordance with certain embodiments, germicidal disinfection apparatus 300 may further comprise a controller 304 and a plurality of emitters 306a-306n. Controller 304 may comprise at least one processing unit 326, at least one memory device 328 and at least one communications chipset 330 configured to receive one or more data inputs and communicate one or more data outputs. In certain embodiments, communications chipset 330 may comprise a wireless transceiver. Communications chipset 330 may be configured to receive one or more external data inputs 318 from, and communicate one or more system data outputs 320 to, one or more networked devices via at least one communications interface. In certain embodiments, memory device 328 may comprise a plurality of instructions stored thereon to command processing unit 326 to perform operations for controlling an emission from emitters 306a-306n. Germicidal disinfection apparatus 300 may further comprise an optical sensor or camera 308, an acoustic transducer 312, and an environmental sensor 314. Optical sensor or camera 308, acoustic transducer or microphone 312, and environmental sensor 314 are configured to receive various environmental signals 316 via various modalities. Environmental signals 316 may comprise any signals generated by a human present within an interior environment. In certain embodiments, optical sensor or camera 308 may be configured to receive light to capture one or more images of occupants within the interior environment. Acoustic transducer 312 may be configured to receive acoustic audio signals from occupants within the interior environment. Environmental sensor 314 may comprise any sensor configured to detect a change in an environment due to the presence of a human, such as a passive infrared sensor, temperature sensor, humidity sensor and $CO_2$ sensor. Germicidal disinfection apparatus 300 may, optionally, comprise a radiation sensor 310 configured to receive reflected radiation 324 reflected from surfaces within the interior environment generated from emitted radiation 322. Environmental signals 316 collected by optical sensor or camera 308, acoustic transducer or microphone 312, and environmental sensor 314, and reflected radiation 324 collected by radiation sensor 310, may be communicated to controller 304 and processed as data inputs by processor 326 according to at least one data processing framework.

In accordance with certain aspects of the present disclosure, controller 304 is operably engaged with emitters 306a-306n to pulse an emission of radiation 322 according to one or more modes of operation. Processor 326 may process environmental signal data 316, external data 318 and/or reflected radiation signal data 324 in real-time to adapt, modify or configure one or more modes of operation or emission parameters for emitters 306a-306n.

Referring now to FIGS. 4A-4D (with reference to FIGS. 2 and 3), functional diagrams 400a-400d illustrating an adaptive germicidal disinfection system are shown. The germicidal disinfection system shown in functional diagrams 400a-400d may comprise germicidal disinfection system 200 as shown in FIG. 2. In accordance with certain aspects of the present disclosure, germicidal disinfection apparatuses 402a-402n are installed on a ceiling of an interior environment 42 (e.g., an airport terminal). Germicidal disinfection apparatuses 402a-402n may comprise germicidal disinfection apparatus 202 as shown in FIG. 2 and/or germicidal disinfection apparatus 300 as shown in FIG. 3. Germicidal disinfection apparatuses 402a-402n may be configured to pulse an emission of light within interior environment 42 according to an operational mode. The emission of light may comprise a single, dual or multi-band emission and may comprise one or a combination of wavelengths within the UV-C spectrum, the visible light spectrum and/or the infrared light spectrum. In accordance with certain embodiments, germicidal disinfection apparatuses 402a-402n may comprise one or more sensors configured to detect signals generated by human occupants 44 present within interior environment 42. In accordance with certain aspects of the present disclosure, germicidal disinfection apparatuses 402a-402n may be configured to receive, in real-time, an acoustic audio input generated by a sneeze or cough 46 from one of the occupants 44 within the interior environment 42. The germicidal disinfection system may be configured to process, in real-time, the acoustic audio input to determine one or more spectral or temporal characteristics of the audio input to identify the audio input as a cough/sneeze 46. The germicidal disinfection system may be configured to further process, in real-time, the audio input to determine an approximate location of the cough/sneeze 46 within the interior environment and identify a zone of emission for one or more of germicidal disinfection apparatuses 402a-402n associated with the approximate location of the cough/sneeze 46 within the interior environment. The germicidal disinfection system may be configured to modulate, in real-time, an emission of radiation from the germicidal disinfection apparatuses (e.g., 402b and 402c) to pulse an emission of UV-C radiation to inactivate airborne pathogens within the respiratory droplets and respiratory nuclei generated by the sneeze/cough 46. In certain embodiments, the emission of UV-C radiation may comprise a wavelength within the Far-UV spectrum (i.e., 207 nm-225 nm) and may further comprise a wavelength of 222 nm. The germicidal disinfection system may pulse the emission of radiation from germicidal disinfection apparatuses 402b and 402c until a timing, dose or emission threshold 404 has been reached or satisfied. Threshold 404 may comprise a determination of an effective "kill dose" to inactivate the airborne pathogens within the respiratory droplets and respiratory nuclei generated by the sneeze/cough 46. Alternatively, threshold 404 may comprise a safety control configured to terminate or modulate the emission of UV-C radiation to prevent occupants 44 from receiving a dose of radiation in excess of a maximum recommended/allowable dose. In accordance with certain aspects of the present disclosure, germicidal disinfection apparatuses 402*a*-402*n* may be communicably engaged with at least one networked server 406 and at least one client device 408 via a network interface. In certain embodiments, server 406 may configured to receive and process data generated by germicidal disinfection apparatuses 402*a*-402*n*. Server 406 may process system data according to one or more data processing framework to configure one or more operational settings for germicidal disinfection apparatuses 402*a*-402*n*. Server 406 may be further configured to process system data according to one or more data machine learning framework to generate one or more recommendations to prevent or mitigate the transmission of disease between occupants 44 within interior environment 42. In accordance with certain aspects of the present disclosure, the one or more recommendations may comprise recommendation for a maximum occupant load/density within interior environment 42 and/or one or more recommendations for the application of chemical cleaning agents to certain target surfaces within interior environment 42. For example, if germicidal disinfection apparatuses 402*a*-402*n* detect a sneeze/cough 46 within interior environment 42 and an effective dose of radiation is delivered to inactivate airborne pathogens but an ineffective dose of radiation has been delivered to inactivate fomite pathogens, the system may generate a recommendation for immediate application of chemical disinfection agents to surfaces within an identified area within interior environment 42. In certain embodiments, system data including the generated infection control recommendation may be communicated from server 406 to client device 408 and presented at a graphical user interface of client device 408. In certain exemplary use cases, client device 408 may be associated with a janitorial technician user. A recommendation generated by the germicidal disinfection system may be communicated to the janitorial technician user comprising an instruction to apply chemical disinfection agents to a specific zone or area within interior environment 42. In other exemplary use cases, client device 408 may be associated with a facilities management user. A recommendation generated by the germicidal disinfection system may be communicated to the facilities management user comprising a recommendation to reduce or restrict an occupant load within a specific zone or area within interior environment 42.

Figure 5:
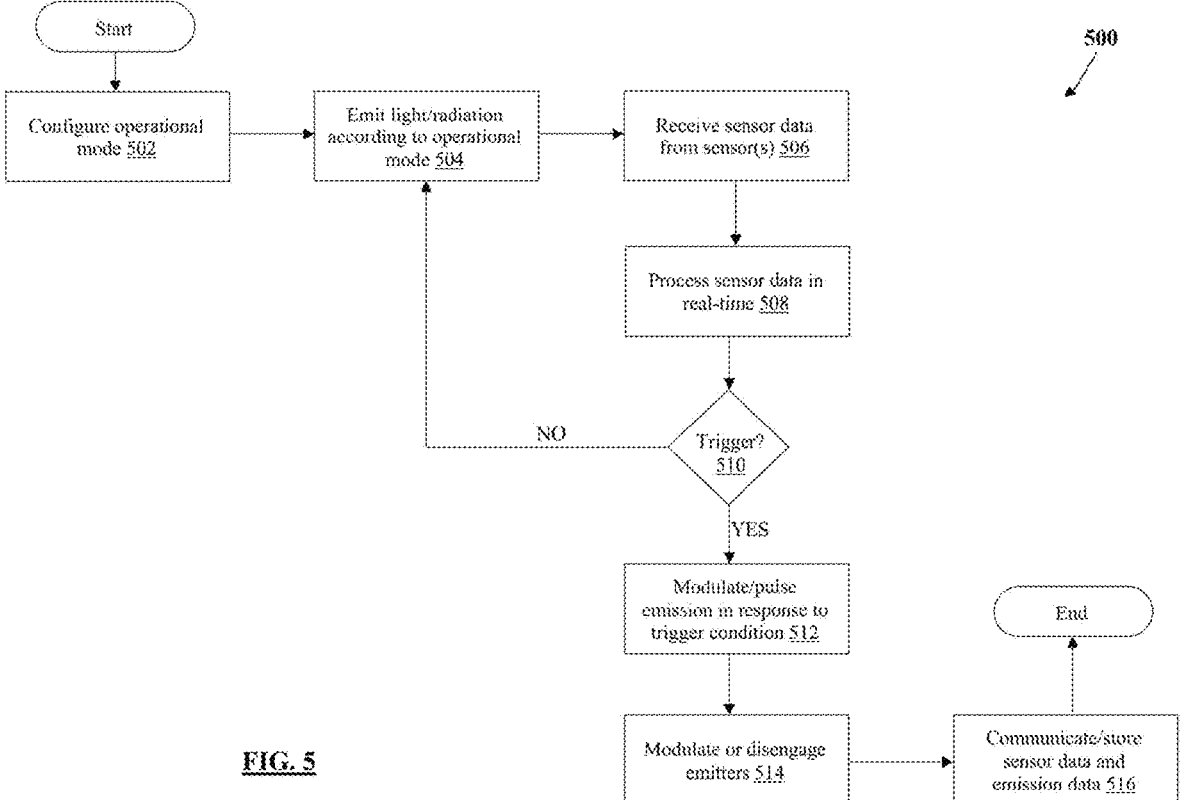
FIG. 5 is a process flow diagram of a routine within an adaptive germicidal disinfection apparatus and system, in accordance with certain aspects of the present disclosure.

Referring now to FIG. 5 (with reference to FIGS. 2 and 3), a process flow diagram of a routine 500 within an adaptive germicidal disinfection apparatus and system is shown. In accordance with certain aspects of the present disclosure, an adaptive germicidal disinfection system may comprise germicidal disinfection system 200 (as shown in FIG. 2) and an adaptive germicidal disinfection apparatus may comprise germicidal disinfection apparatus 202 (as shown in FIG. 2) and/or germicidal disinfection apparatus 300 (as shown in FIG. 3). Routine 500 may be embodied within one or more processor-executable instructions of controller 204 (as shown in FIG. 2) and/or controller 304 (as shown in FIG. 3) and/or one or more processor-executable instructions of local server 216 (as shown in FIG. 2) and/or one or more processor-executable instructions of remote server 226 (as shown in FIG. 2). Routine 500 may be executed locally, remotely or a combination thereof. In accordance with certain aspects of the present disclosure, routine 500 may comprise one or more operations for controlling and/or modulating an emission of UV-C radiation from one or more emitters in response to processing one or more signals generated by one or more human occupants present within an interior environment in real-time. In accordance with certain aspects of the present disclosure, routine 500 may be initiated by configuring, with a germicidal disinfection apparatus, an operational mode for one or more emitters (Step 502). Routine 500 may continue by executing one or more operations for emitting visible light and/or UV-C radiation from the one or more emitters according to the configured operational mode (Step 504). Routine 500 may continue by executing one or more operations for receiving sensor data from one or more sensors (Step 506) and processing the sensor data in real-time according to at least one data processing framework (Step 508). In certain embodiments, the sensors may comprise one or more optical sensor or camera, acoustic transducer or microphone, and/or environmental sensor; for example, the sensors as shown and described in FIGS. 2 and 3. Routine 500 may continue by executing one or more data processing operations to determine the existence of at least one trigger condition for the interior environment based on the sensor data (Step 510). In certain embodiments, a trigger condition may be associated with one or more risk factors for person-to-person transmission of at least one pathogen (e.g., the COVID-19 virus). For example, a trigger condition may comprise the identification of a cough or a sneeze within an interior environment, an analysis of body temperature of one or more occupants within an interior environment, a temperature or humidity level within an interior environment, and/or an occupant load or density (i.e., "social distancing") within an interior environment over a specified period of time. If the output of Step 510 is NO (i.e., the sensor data is not indicative of a trigger condition), then routine 500 continues to emit visible light and/or UV-C radiation from the one or more emitters according to the configured operational mode in Step 504. If the output of Step 510 is YES (i.e., the sensor data is indicative of a trigger condition), then routine 500 proceeds to execute one or more operations to modulate an output of the one or more emitters and pulse radiation from the one or more emitters in response to control logic associated with the specific trigger condition (Step 512). Routine 500 continues by executing the one or more operations to pulse radiation from the one or more emitters and proceeds by further modulating or disengaging the output of the one or more emitters in accordance with the control logic (Step 514). Routine 500 continues by executing one or more data processing operations to store sensor data and emission data in local or remote memory and/or communicating the sensor data and/or emission data to the local or remote server for further data processing and/or data storage (Step 516).

Figure 6:
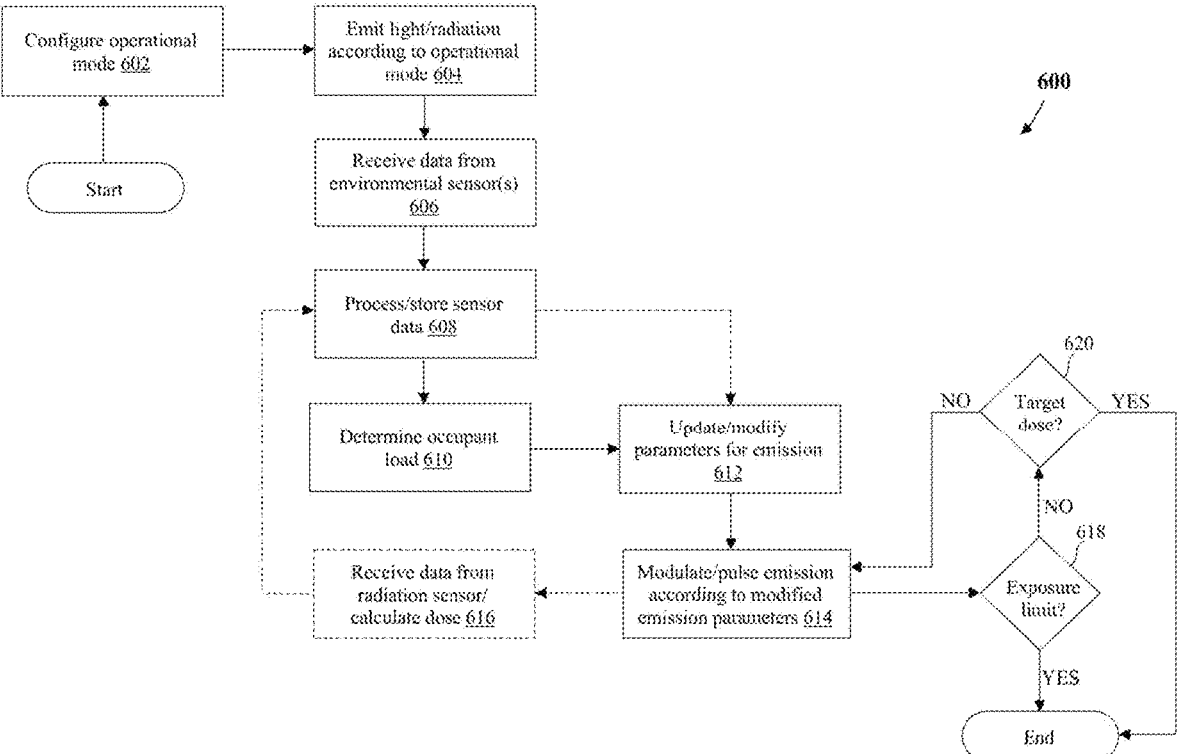
FIG. 6 is a process flow diagram of a routine within an adaptive germicidal disinfection apparatus and system, in accordance with certain aspects of the present disclosure.

Referring now to FIG. 6, a process flow diagram of a routine 600 within an adaptive germicidal disinfection apparatus and system is shown. In accordance with certain aspects of the present disclosure, an adaptive germicidal disinfection system may comprise germicidal disinfection system 200 (as shown in FIG. 2) and an adaptive germicidal disinfection apparatus may comprise germicidal disinfection apparatus 202 (as shown in FIG. 2) and/or germicidal disinfection apparatus 300 (as shown in FIG. 3). Routine 600 may be embodied within one or more processor-executable instructions of controller 204 (as shown in FIG. 2) and/or controller 304 (as shown in FIG. 3) and/or one or more processor-executable instructions of local server 216 (as shown in FIG. 2) and/or one or more processor-executable instructions of remote server 226 (as shown in FIG. 2). Routine 600 may be executed locally, remotely or a combination thereof and/or may comprise a sub-routine of routine 500 and/or may utilize one or more outputs of routine 500. In accordance with certain aspects of the present disclosure, routine 600 may be initiated by configuring, with a germicidal disinfection apparatus, an operational mode for one or more emitters (Step 602). Routine 600 may continue by executing one or more operations for emitting visible light and/or UV-C radiation from the one or more emitters according to the configured operational mode (Step 604). Routine 600 may continue by executing one or more operations for receiving sensor data from one or more environmental sensors (Step 606). Routine 600 may proceed by executing one or more data processing operations for processing and storing the sensor data from the one or more environmental sensors (Step 608). Routine 600 may continue by determining an occupant load for one or more zones within an interior environment based on the processed output from Step 608 (Step 610). Routine 600 may continue by executing one or more operations to update or modify one or more parameters or control settings for emission of UV-C radiation from the one or more emitters for the configured operational mode (Step 612). Routine 600 may continue by executing one or more operations for modulating an emission of UV-C radiation from the one or more emitters according to the output of Step 612 (Step 614). Routine 600 may further comprise one or more operations for determining whether a target dose has been delivered by the one or more emitters (Step 620) or a radiation exposure limit has been reached for one or more occupants within the interior environment (Step 618). In certain embodiments, if the output of Step 618 is YES (i.e., an exposure limit has been reached), then routine 600 is concluded by terminating the emission of UV-C radiation within the zone of emission. If the output of Step 618 is NO (i.e., an exposure limit has not been reached), then routine 600 continues by executing decision step 620. In certain embodiments, if the output of Step 620 is YES (i.e., a target dose has been delivered), then routine 600 is concluded by terminating or reducing the emission of UV-C radiation within the zone of emission. If the output of Step 620 is NO (i.e., a target dose has not been delivered), then routine 600 continues to modulate/emit radiation in accordance with Step 614. In certain embodiments, routine 600 may, optionally, comprise one or more steps for receiving data from at least one radiation sensor in order to calculate a dose of radiation delivered by the one or more emitters to the interior environment (Step 616).

Figure 7:
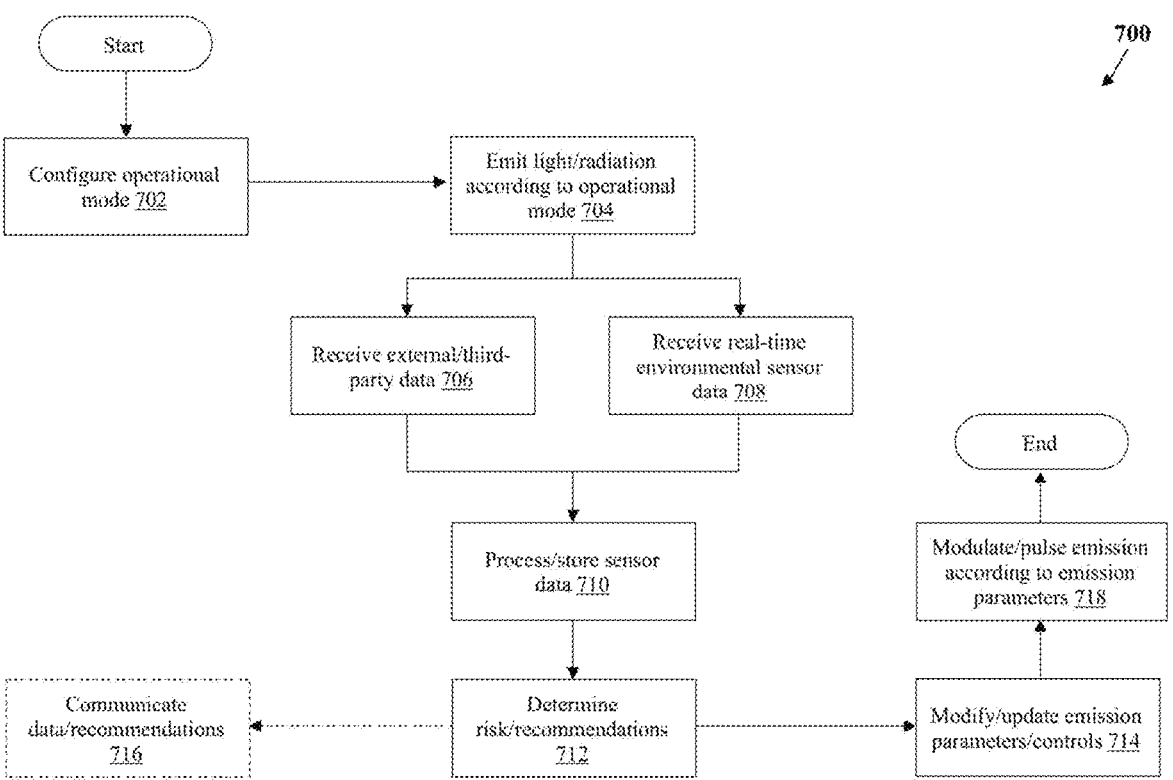
FIG. 7 is a process flow diagram of a routine within an adaptive germicidal disinfection apparatus and system, in accordance with certain aspects of the present disclosure.

Referring now to FIG. 7, a process flow diagram of a routine 700 within an adaptive germicidal disinfection apparatus and system is shown. In accordance with certain aspects of the present disclosure, an adaptive germicidal disinfection system may comprise germicidal disinfection system 200 (as shown in FIG. 2) and an adaptive germicidal disinfection apparatus may comprise germicidal disinfection apparatus 202 (as shown in FIG. 2) and/or germicidal disinfection apparatus 300 (as shown in FIG. 3). Routine 700 may be embodied within one or more processor-executable instructions of controller 204 (as shown in FIG. 2) and/or controller 304 (as shown in FIG. 3) and/or one or more processor-executable instructions of local server 216 (as shown in FIG. 2) and/or one or more processor-executable instructions of remote server 226 (as shown in FIG. 2). Routine 700 may be executed locally, remotely or a combination thereof and/or may comprise a sub-routine of routine 500 and/or routine 600 and/or may utilize one or more outputs of routine 500 and/or routine 600. In accordance with certain aspects of the present disclosure, routine 700 may be initiated by configuring, with a germicidal disinfection apparatus, an operational mode for one or more emitters (Step 702). Routine 700 may continue by executing one or more operations for pulsing an emission of visible light and/or UV-C radiation from the one or more emitters according to the configured operational mode (Step 704). Routine 700 may continue by executing one or more operations for receiving one or more external and/or third-party data inputs (Step 706) and/or receiving real-time environmental sensor data inputs (Step 708). Routine 700 comprise one or more data processing operations for processing the data received in Step 706 and Step 708 according to at least one data processing framework and storing the data in at least one database (Step 710). In certain embodiments, the at least one data processing framework comprises at least one machine learning framework. Routine 700 may further comprise one or more operations for determining a degree of disease transmission risk and/or one or more infection control recommendations based on the output of Step 710 (Step 712). Routine 700 may optionally comprise one or more operations for communicating an output of Step 710 and/or Step 712 to one or more of a local server, a remote server and/or a client device. Routine 700 may continue by executing operations for modifying or updating one or more emission parameters and/or controls (Step 714) and executing operations for modulating or pulsing an emission of radiation from the one or more emitters according to the updated or modified emission parameters (Step 718). In accordance with certain embodiments, controller 204 (as shown in FIG. 2) and/or controller 304 (as shown in FIG. 3) and/or one or more processor-executable instructions of local server 216 (as shown in FIG. 2) and/or one or more processor-executable instructions of remote server 226 (as shown in FIG. 2) may be communicably engaged with one or more third-party servers (e.g., the Center for Disease Control and Prevention (CDC)) to receive a public health data input associated with a rate or prevalence of transmission of at least one microorganism in a geographic location associated with the adaptive germicidal disinfection apparatus and system (e.g., disease activity data). For example, if the adaptive germicidal disinfection apparatus and system is installed in an airport located in a specific city (e.g., Chicago, Illinois), one or more elements of the adaptive germicidal disinfection apparatus and system may be communicably engaged with the one or more third-party servers (e.g., CDC servers) to receive public health data (e.g., disease activity data) associated with the specific city (e.g., COVID-19 activity data in Chicago, Illinois). The adaptive germicidal disinfection apparatus and system may be configured to process the public health data to configure, modify and/or update one or more emission parameters and/or controls of the adaptive germicidal disinfection apparatus and system. For example, if the public health data is indicative of a certain rate of transmission of a specific pathogen in a location of the adaptive germicidal disinfection apparatus and system (e.g., COVID-19 activity data in Chicago, Illinois), the adaptive germicidal disinfection apparatus and system may configure, modify and/or update one or more emission parameters and/or controls according to the public health data. In accordance with certain aspects of the present disclosure, configuring, modifying and/or updating the one or more emission parameters and/or controls may include, but is not limited to: configuring an occupancy density threshold (i.e., "social distancing") for one or more locations within an interior environment; configuring one or more emission wavelengths and/or combination of emission wavelengths for one or more emitters; configuring one or more risk factors, including emission event factors (e.g., coughing/sneezing), occupant risk factors (e.g., occupant body temperature thresholds); configuring a duration and intensity (i.e., radiation dosage) for one or more locations within an interior environment; and establishing one or more "no-go zones" within an interior environment (i.e., designated restricted areas within an environment that require germicidal disinfection before normal use or occupancy may resume).

Referring now to FIG. 8, a process flow diagram of a method 800 for adaptive germicidal disinfection of an interior environment is shown. In accordance with certain aspects of the present disclosure, method 800 may comprise configuring a germicidal disinfection apparatus within an interior environment (Step 802). In accordance with certain aspects of the present disclosure, an adaptive germicidal disinfection apparatus may comprise germicidal disinfection apparatus 202 (as shown in FIG. 2) and/or germicidal disinfection apparatus 300 (as shown in FIG. 3). Method 800 may proceed by engaging one or more emitters for the germicidal disinfection apparatus according to an operational mode of the germicidal disinfection apparatus (Step 804). Method 800 may proceed by receiving at least one sensor input comprising data indicative of at least one environmental condition within the interior environment (Step 806). In accordance with various embodiments, the at least one environmental condition may comprise at least one condition associated with the presence of a human occupant within the interior environment (for example, a sneeze or a cough emanated from a human occupant). Method 800 may proceed by processing, in real-time, the at least one sensor input according to at least one data processing framework and/or machine learning framework to determine one or more emission parameters for the germicidal disinfection apparatus (Step 808). Method 800 may proceed by engaging the one or more emitters to pulse an emission of radiation in accordance with the one or more emission parameters determined in Step 808 (Step 810).

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that phases of the processes described herein may be performed in orders different than those illustrated in the flowcharts. In other words, the processes represented by the blocks of a flowchart may, in some embodiments, be performed in an order other than the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A germicidal disinfection apparatus comprising:
a housing configured to be selectively coupled to a surface of an interior room of a building;
a plurality of emitters housed within the housing, the plurality of emitters comprising at least one emitter configured to emit ultraviolet radiation at a wavelength in the range of 200 nm to 405 nm;
one or more sensors housed within the housing, the one or more sensors comprising at least one occupancy sensor or environmental condition sensor; and
a controller housed within the housing and operably coupled to the plurality of emitters and the one or more sensors, the controller comprising a non-transitory memory storing a control protocol,
wherein the controller is configured to:
receive, in real time, sensor input from the one or more sensors;

process the sensor input in accordance with the control protocol to automatically determine at least one risk factor for person-to-person transmission of at least one microorganism;
in response to the determination, automatically control the plurality of emitters to emit ultraviolet radiation having a wavelength, intensity, duty cycle, and/or emission pattern selected to deliver a germicidal dose to a target zone within the interior room,
wherein the controlling comprises physically modulating at least one of the wavelength or duty cycle during the emission;
calculate, during operation, a radiation exposure limit for one or more sensed occupants within the interior room; and
automatically disengage at least a portion of the plurality of emitters when the radiation exposure limit has been reached.

2. The apparatus of claim 1 wherein the one or more sensors are selected from the group consisting of cameras, acoustic transducers, microphones, radiation sensors, passive infrared sensors, temperature sensors, humidity sensors and carbon dioxide sensors.

3. The apparatus of claim 1 wherein determining the at least one risk factor for person-to-person transmission of at least one microorganism comprises processing, with the controller, the input from the one or more sensors to determine an occupant density for the interior room of the building and wherein the controller modulates at least one of wavelength, duty cycle, intensity, or emitter subset in response to the determined occupant density.

4. The apparatus of claim 1 wherein determining the at least one risk factor comprises determining an occurrence of a microorganism transmission event within the interior room of the building,
wherein the microorganism transmission event comprises a cough or sneeze from at least one occupant present in the interior room of the building and wherein the controller directs ultraviolet emission to a localized target zone associated with the detected event.

5. The apparatus of claim 3 wherein the controller automatically increases germicidal dose output, by modulating intensity and/or duty cycle, in response to the occupant density for the interior room of the building exceeding a predetermined threshold value.

6. The apparatus of claim 1 wherein the plurality of emitters comprises a first emitter configured to pulse a first emission of ultraviolet radiation at a first wavelength in the range of 200 nm to 405 nm and a second emitter configured to pulse a second emission of ultraviolet radiation at a second wavelength in the range of 200 nm to 405 nm, wherein the first wavelength is different from the second wavelength, and wherein the controller alternates or simultaneously drives the first and second emitters to provide a composite germicidal dose profile.

* * * * *